(12) United States Patent
Hasik et al.

(10) Patent No.: US 8,027,575 B2
(45) Date of Patent: Sep. 27, 2011

(54) HEATER CONTACT ASSEMBLY FOR VOLATILE LIQUID DISPENSER

(75) Inventors: Sebastian D. Hasik, Antioch, IL (US); Richard L. Norwood, Racine, WI (US); John T. Filiczkowski, Spring Grove, IL (US); Joel E. Adair, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 812 days.

(21) Appl. No.: 12/023,574

(22) Filed: Jan. 31, 2008

(65) Prior Publication Data

US 2009/0196586 A1 Aug. 6, 2009

(51) Int. Cl.
*A61H 33/06* (2006.01)
*F24F 6/00* (2006.01)

(52) U.S. Cl. ........................................ 392/394; 392/392

(58) Field of Classification Search .......... 392/386–406, 392/324–337; 237/78; 126/113, 20–20.2
See application file for complete search history.

(56) References Cited

U.S. PATENT DOCUMENTS

| | | | | |
|---|---|---|---|---|
| 2,821,613 A * | 1/1958 | Sullivan | ........................ | 392/400 |
| 2,830,672 A * | 4/1958 | Asker | ............................. | 96/144 |
| 2,880,527 A * | 4/1959 | Merry | ............................. | 37/248 |
| 4,406,785 A | 9/1983 | Siefer | | |
| 4,574,187 A | 3/1986 | Crews et al. | | |
| 4,789,850 A | 12/1988 | Sepso et al. | | |
| 4,871,115 A * | 10/1989 | Hessey | ........................... | 239/136 |
| 4,874,924 A * | 10/1989 | Yamamoto et al. | ........... | 392/395 |
| 4,973,934 A | 11/1990 | Saito et al. | | |
| 5,142,265 A | 8/1992 | Motoyoshi et al. | | |
| 5,556,192 A * | 9/1996 | Wang | ............................. | 362/276 |
| 5,940,577 A | 8/1999 | Steinel | | |
| 6,374,045 B2 | 4/2002 | Millan | | |
| 6,411,776 B1 | 6/2002 | Millan | | |
| 6,487,367 B2 | 11/2002 | Vieira | | |
| 6,567,613 B2 | 5/2003 | Rymer | | |
| 6,968,124 B1 | 11/2005 | Varanasi et al. | | |
| 7,012,225 B2 * | 3/2006 | Bohlender et al. | ............. | 219/536 |
| 7,086,607 B2 | 8/2006 | Bresolin et al. | | |
| 7,288,748 B1 * | 10/2007 | Thuot | ........................... | 219/541 |
| 2007/0001800 A1 | 1/2007 | Kambara | | |
| 2009/0196586 A1 * | 8/2009 | Hasik et al. | ................... | 392/394 |

FOREIGN PATENT DOCUMENTS

| | | |
|---|---|---|
| EP | 0290159 A | 11/1988 |
| EP | 0965267 A | 12/1999 |
| EP | 0998947 A | 5/2000 |
| EP | 1348446 A | 10/2003 |
| EP | 1372161 | 12/2003 |
| WO | 97/02054 A | 1/1997 |
| WO | WO 2006/046209 | 5/2006 |

OTHER PUBLICATIONS

A page of drawings and depictions of the "All-Out" heater engine, undated, admitted prior art.
PCT/US2009/000526 International Search Report and Written Opinion dated Aug. 26, 2009.

* cited by examiner

*Primary Examiner* — Daniel L Robinson

(57) ABSTRACT

Disclosed herein are heaters for dispensing volatile air treatment chemicals. Semi-circular electrical contacts are provided in a ring-type heater, and alignment and anchoring features are provided to facilitate use of a spring to accommodate thermal expansion.

10 Claims, 4 Drawing Sheets

HEATER CONTACT ASSEMBLY FOR VOLATILE LIQUID DISPENSER

CROSS-REFERENCE TO RELATED APPLICATIONS

Not Applicable.

STATEMENT REGARDING FEDERALLY SPONSORED RESEARCH/DEVELOPMENT

Not Applicable

BACKGROUND OF THE INVENTION

The present invention relates to heaters used to dispense air treatment chemicals, such as insect control agents, fragrances and deodorizers. More particularly, it relates to contact assemblies for carrying electricity to a heating element used therewith, and for then spreading the heat generated by the heating element around a dispensing wick.

A known type of air treatment chemical dispenser is that disclosed in U.S. Pat. No. 6,968,124, the disclosure of which is incorporated by reference. In this type of dispenser a liquid air treatment chemical is stored in a bottle. A wick dips into the liquid, and then extends upward out of the bottle. An upward end of the wick is surrounded by a ring-type electrical heater. Heating of the upward end of the wick causes air treatment chemical to be volatized from the wick, and thus the bottle, to the surrounding area.

One particularly desirable form of ring-type heater is one with a positive temperature coefficient "PTC" heating element. A PTC heating element is typically in the form of a pill-shaped tablet formed from pressed conductive granular material. Its resistivity to electrical charge generates heat, but that resistivity increases with an increase in temperature, thereby providing an inherent desirable control function against overheating.

A particularly desirable form of heater that uses a PTC heating element is the "All-Out" heater sold in India by Karamchand Appliances Pvt. Ltd. This product has a housing that is generally doughnut shaped, but hollow. A first ring-shaped electrical contact is positioned in the housing to extend around a central axial through bore, the bore being sized to receive the wick. One end of the contact connects to a prong of an external plug. At the other end there is a portion designed to abut a PTC type pill heating element.

On the other side of the PTC pill of the All-Out heater is placed a second ring-shaped electrical contact that also extends around the through bore. It has a connection to another external plug at one end. At the other end of the ring there is a portion designed to rest against an opposed side of the PTC pill. A top housing part is riveted to the lower housing part.

Electrical charge passes through the contacts of the All-Out heater to the pill, causing the pill to generate heat. The generated heat is then carried back along the contact to spread the heat around the through bore, and then to the wick. Heating of the wick facilitates volatilization of air treatment chemicals drawn up by the wick.

While this type of heater has many advantages, there are still a number of features in need of improvement. For example, because the two ring contacts are over each other in close proximity all the way around the ring, there is a theoretical potential for charge to be directed inefficiently if the parts are not precisely assembled. Further, the way some of the parts are installed inside the housing in the All-Out design is awkward, particularly with respect to insuring that small parts are properly aligned for optimal function. Also, the need to rivet the housing together adds cost and complexity.

Hence, a need exists for an improved heater for use with such volatile dispensers.

BRIEF SUMMARY OF THE INVENTION

The present invention provides a heater suitable for use with an air treatment chemical dispenser. The heater has a housing with a base and a cover. The base and cover together define an internal generally ring-shaped cavity and an axial through bore.

There are first and second arc-shaped electrical contacts positioned in the cavity, with the second arc-shaped electrical contact having a portion overlapping the first arc-shaped electrical contact, and having another portion which does not overlap the first arc-shaped electrical contact. There is also a heating element sandwiched between the first and second electrical contacts at a position where the first and second electrical contacts overlap. The first and second arc-shaped electrical contacts do not overlap over a majority of the first arc-shaped electrical contact.

The contacts provide the appropriate electrical energy to the heating element. However, according to the present invention, those parts not separated by the heating element are kept quite far apart. This reduces the theoretical potential for short circuiting or arcing. To further minimize the risk of short circuiting even adjacent the heating element, at least one of the first and second electrical contacts can be formed with a raised platform/nose adjacent the heating element.

The first and second electrical contacts are preferably made of a metal such as aluminum which is both electrically conductive and heat conductive. Thus, they can carry energy from wall plugs to the heating element, and then carry heat back around the through bore.

In other refinements, at least one of the first and second electrical contacts can be formed with a portion that bends in an axial direction along the through bore so as to carry heat along a greater portion of the wick. There can also be a spring positioned adjacent at least one of the first and second electrical contacts to bias that contact towards the heating element while also allowing for adjustment if thermal expansion of the housing occurs when the heating element is generating heat.

The contacts extend on opposite sides of the through bore, for almost a total circumference. At least one of the first and second electrical contacts can have an alignment notch which interfits with an alignment projection from the housing, and the spring can have an alignment notch that interfits with that same alignment projection of the housing. In this manner, the parts can be properly positioned for optimal heat and energy transfer.

There may be a crimping terminal at a distal end of both contacts, and at a proximal end of both contacts there may be generally circular contact portions for sandwiching the heating element. While a variety of resistance heating elements can be used, it is highly preferred to use a positive temperature coefficient pill-shaped heating element. For example, there could be a pill-shaped ceramic portion having first and second opposed facing surfaces, a first conductive layer formed on the first facing surface, and a second conductive layer formed on the second facing surface.

To insure proper alignment there can be provided an alcove that radially extends off the main cavity. It is also preferred to have the base and cover be welded together to enclose the internal parts and hold them in proper alignment.

In another aspect the invention provides a spring (made of a thin flexible metal such as steel) for biasing an electrical contact against a positive temperature coefficient heating element. It has a flat head contact portion, a forwardly arced body belly portion extending from the head portion, two flat leg portions extending from the body portion to define an alignment notch there between, and a rearwardly projecting foot portion.

In another aspect the invention provides an electrical contact suitable for use with a positive temperature coefficient heating element. The electrical contact has a head with an axially extending nose formed thereon, a flat arc-shaped body extending from the head, the body also having an axially projecting belly portion, a leg extending from the body, and an electrical crimping terminal in the form of a foot mounted on the leg.

Heaters of the present invention are designed to surround a wick extending from a bottle or other reservoir containing an air treatment chemical. The overall heater, once assembled, looks almost doughnut-like, with its generally central hole providing a position for the wick to pass into.

The electrical contacts are linked to plugs, which a consumer can then plug into a wall outlet or the like. The electricity provided through the contacts generates heat via the PTC heating element. That heat is then conducted essentially entirely around the through bore, and thus essentially entirely around the wick.

The assembly can accommodate thermal expansion of the outer housing, Even if the outer housing expands during heating the contacts will be biased by the spring into good electrical and thermal contact. Also, the electrical contacts will be kept sufficiently far apart, thereby reducing risks of short circuiting or the like.

Various embodiments of the present invention have other advantages as well. For example, in some embodiments the parts can be more easily assembled, and the welding together of the outer housing parts avoids the need for riveting.

The foregoing and other advantages of the present invention will be apparent from the following description. In the description that follows, reference is made to the accompanying drawings which form a part thereof, and in which there is shown by way of illustration, and not limitation, a preferred embodiment of the invention. As this embodiment is merely illustrative, it is not intended to represent the full scope of the invention. Thus, reference should therefore be made to the claims herein for interpreting the scope of the invention.

BRIEF DESCRIPTION OF THE DRAWINGS

FIG. 1 is an exploded perspective view of a heater constructed in accordance with the present invention, shown adjacent a wicked bottle that it can be used with;

DETAILED DESCRIPTION OF THE INVENTION

Figure 1:
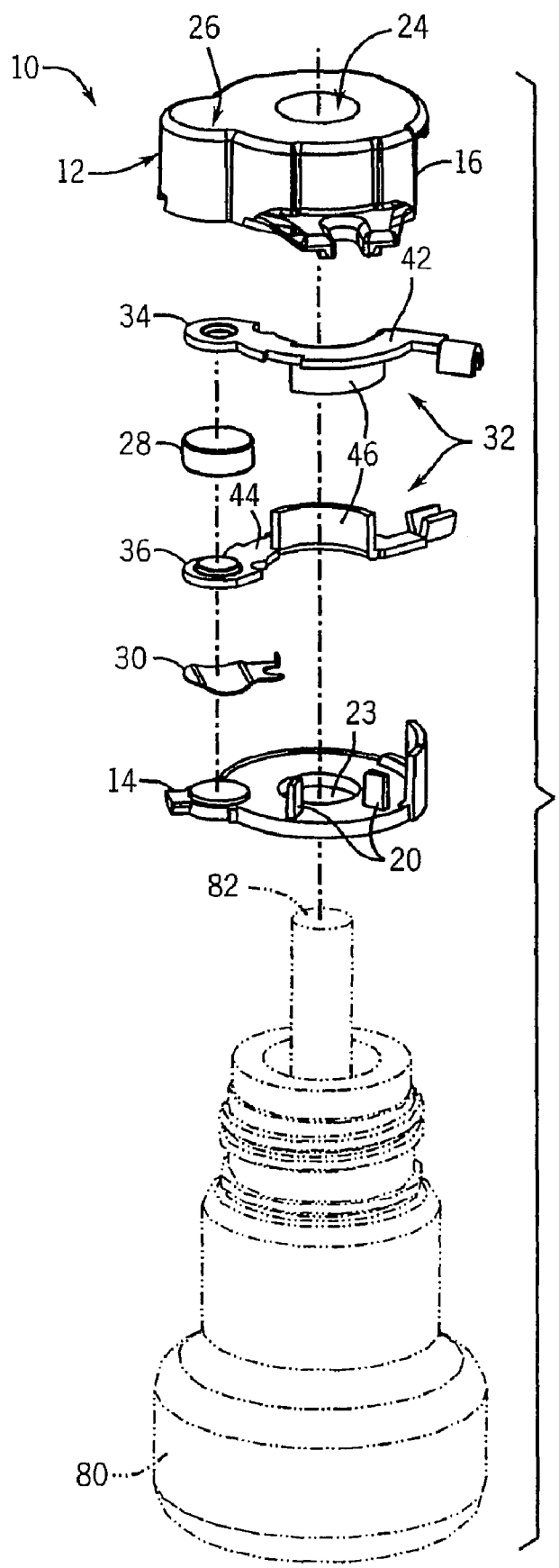
Figure 2:
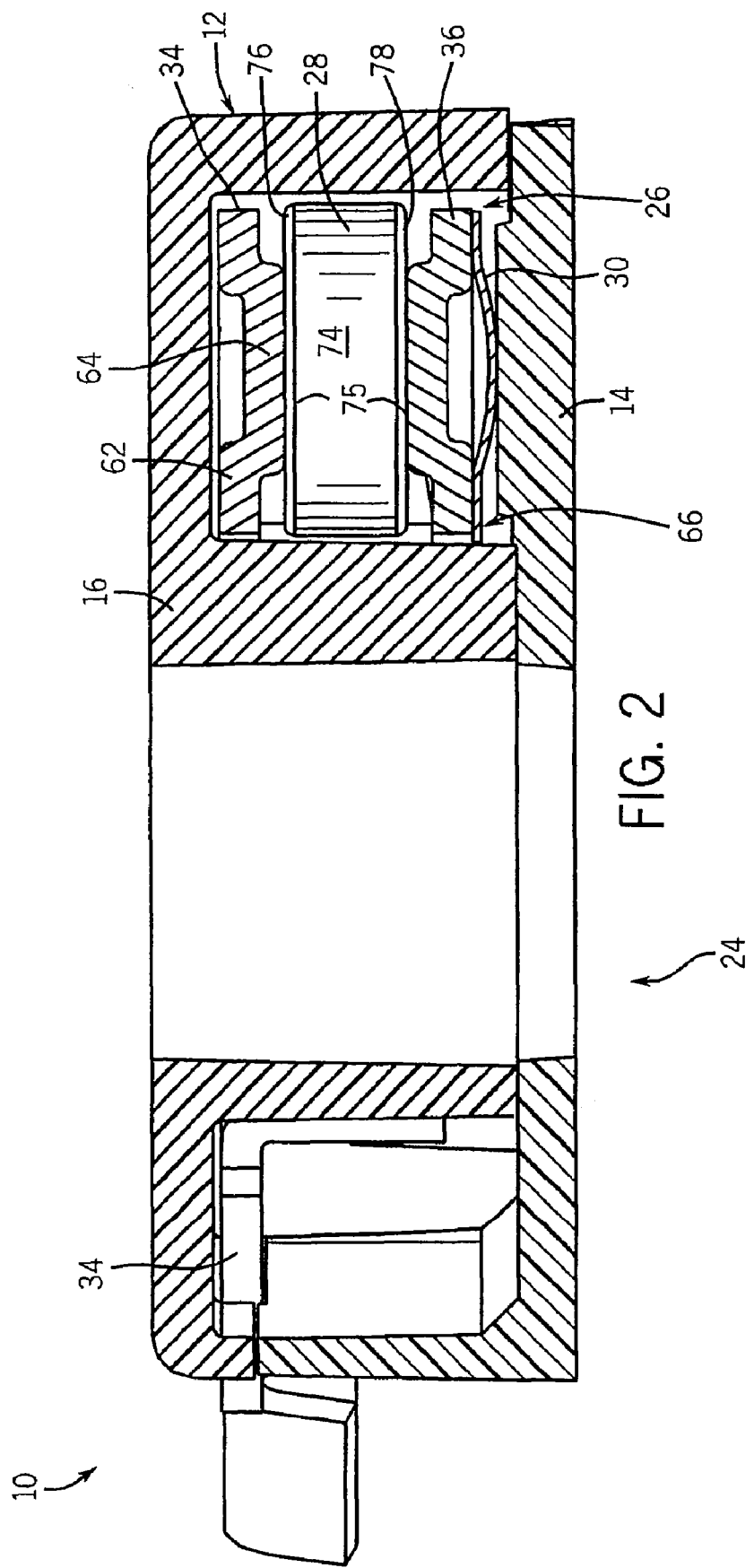
FIG. 2 is a cross-sectional view of the assembled heater of FIG. 1.
Figure 3:
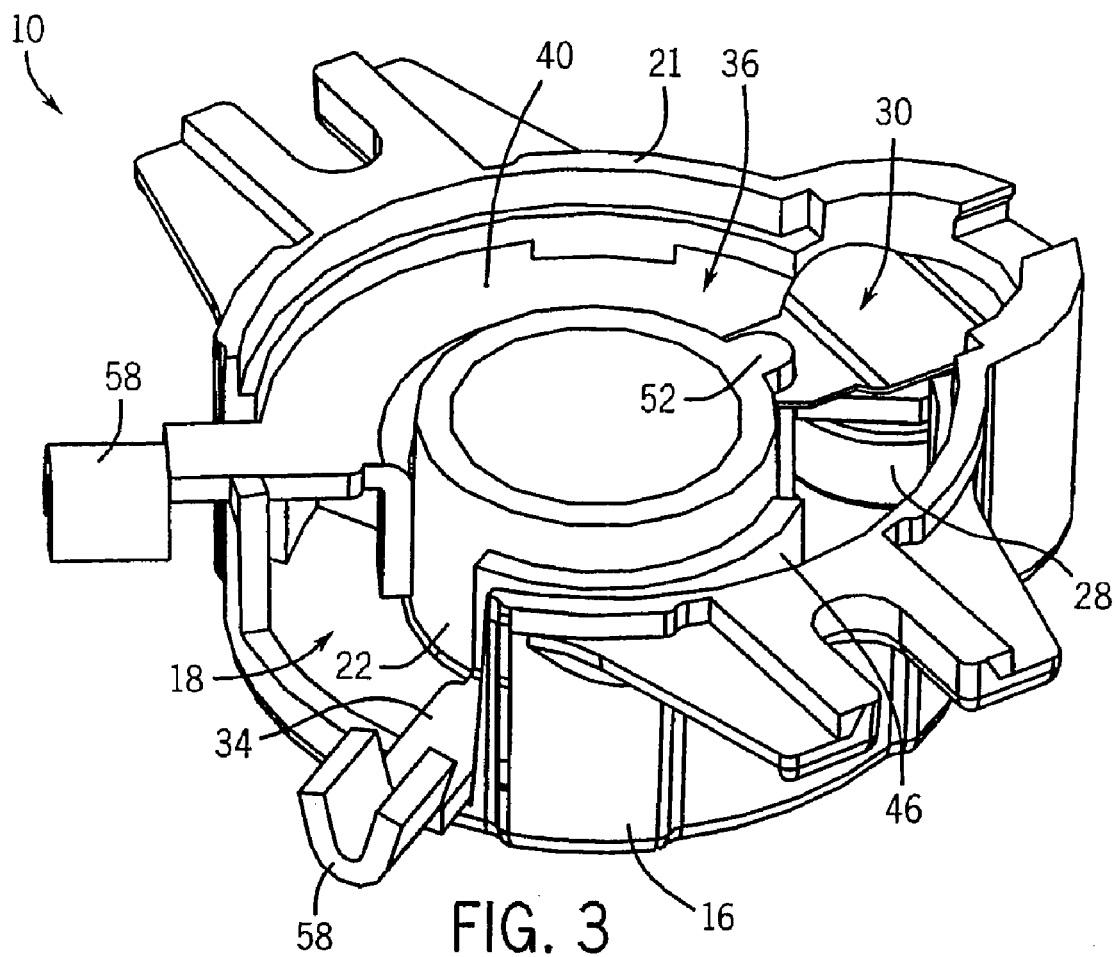
FIG. 3 is a bottom perspective view of the heater of FIG. 1, with its base removed for ease of illustration.

Turning first to FIGS. 1-3, there is shown a heater 10 that has a housing 12 formed of a base 14 and a cover 16. For the convenience of description, the direction towards the cover 16 will be referred to as "up" even though in actual use the heater 10 may be used in any orientation. Of course, when a conventional wick is used it is preferred to have the FIG. 1 directionality to avoid the wick exhausting the active too quickly.

The heater 10 is designed to have its through bore 24 accommodate wick 82 of a conventional container 80 that stores a supply of liquid air treatment chemical. As an example, the liquid could be a hydrocarbon solvent containing a small amount of an insect control active such as pyrethrum, and the wick could be a sand-type wick. The housing 12 is preferably injection molded from a plastics material having low thermal expansion properties, such as Zytel® from DuPont, a 25% glass fiber reinforced, flame retardant polyamide resin.

The cover 16 includes a generally circular outer wall 21 and a circular inner wall 22. The base 14 has a hole 23 formed therein that aligns with the inner wall 22 of the cover 16 to create a through-hole or bore 24 in the housing 12. An annular interior cavity 18 is defined by the base 14 and cover 16 and houses the primary electrical components of the heater 10.

Once the internal parts are installed, base 14 and cover 16 are preferably sonically welded together to seal the housing 12 and prevent a consumer from intentionally or inadvertently accessing the electrical components contained therein. Other welding techniques may be used instead.

The housing 12 defines an alcove 26 wherein at least portions of a PTC heating element 28, a spring 30 and contacts 32 are seated therein. Specifically with respect to the contacts, each is arc-like (and almost semicircular). There is an upper or first contact 34 and a lower or second contact 36. They sandwich a PTC heating element 28, with the second contact 36 being biased towards the PTC heating elements 28 by spring 30. As shown, the spring 30 is located below the second contact 36.

The heating element 28 may be any conventional heating device (e.g. various types of resistance heaters). However, a highly preferred heating element is a PTC device as previously discussed. The PTC heating element 28 shown is formed into a "pill" shape, i.e., a flattened cylinder having a circular footprint, although other appropriate shapes could be used as well. The heating element 28 is comprised of resistive material 70, for example, a ceramic, formed into a pill-shape with a film of conductive material 75 applied to the top and bottom surface of the resistive material 74, thereby creating a pair of electrodes 76, 78 for the heating element 28.

When assembled into the housing 12, one positions the first contact 34 against the top wall of the cover. One then places the pill-shaped heating element 28 against a nose-shaped platform of a head-shaped portion of the contact. The body of the first contact then extends along the side of the annular cavity. One then positions the second contact 36 on the second face of the pill-shaped heating element 28, with the main body of the contact then extending on an opposed side of the annular cavity from the first contact. Then, the spring 30 is positioned between the second contact 36 and the base.

As a result, a generally circular belly portion 66 of the spring 30, and head portions of the first and second contacts 34, 36 are located within the alcove 26. Both contacts 34, 36 are placed in direct contact with the heating element 28. The contacts 34, 36 are preferably made of aluminum so as to provide an efficient electrical path and good heat conductivity.

Each contact 32 is comprised of a flat main body 40 arced at 42 and 44 to define a radially inner edge 45 and a radially outer edge 47. The curvature of the inner edge 45 corresponds to the curvature of the inner wall 22 while the curvature of the outer edge 47 corresponds to the curvature of the outer wall 21. Vertically extending supports 20 formed in the housing 12 help keep the contacts 34, 36 in place and provide additional support against crushing forces.

The contacts have axially extending portions 46 in the form of bellies that abut the through bore 24 area. This helps transfer additional heat to the wick, while reducing the amount of heat that reaches back to the terminals 58.

A distal leg 54 of the contact 32 includes a radially extending wire connection foot 56 that has a u-shaped crimping terminal 58. Electrical wiring (not shown) is connected thereto by crimping the terminal 58 onto the wire. The electrical wiring is further connected to plugs (not shown) that are suitable to plug into a typical electrical outlet. Such plugs are well known in the art, and depending on the electrical supply and country involved, will take appropriate configurations to permit the device to be plugged into a room electrical supply.

A head 60 of each contact 32 includes a circular engaging portion 62 configured to be seated within the alcove 26. The engaging portion 62 includes a raised circular platform or nose 64.

As shown in FIG. 2, when the components are assembled together to form the heater 10, the platform 64 of the upper contact 34 is held in direct contact with the upper electrode 76. The platform 64 of the lower contact 36 is held in direct contact with the lower electrode 78 of the heating element 28.

Each contact 32 further includes a notch 48 cut into the radially outer edge 47 and configured to mate with an alignment tab 50 formed in the cover 16 of the housing 12. A second, semi-circular, notch 71 is located adjacent the engaging portion 62 and configured to mate with a second, semi-circular projection 52 formed in the inner wall 22. Both tabs/projections 50, 52 help ensure that the contacts 34, 36 are aligned properly and secured within the housing 12.

Figure 6:
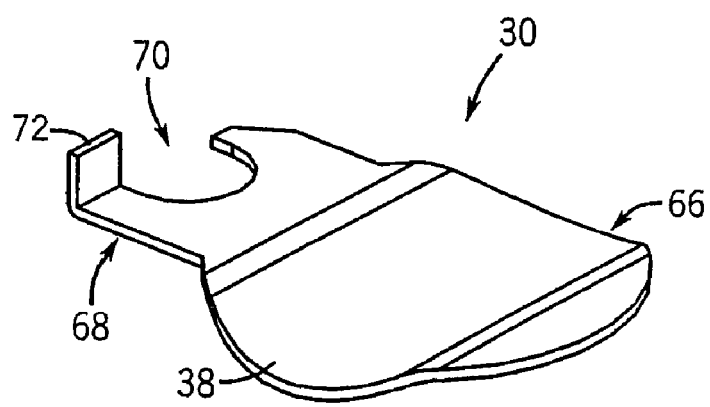
FIG. 6 is an enlarged perspective view of a spring used with the FIG. 1 heater.
Figure 4:
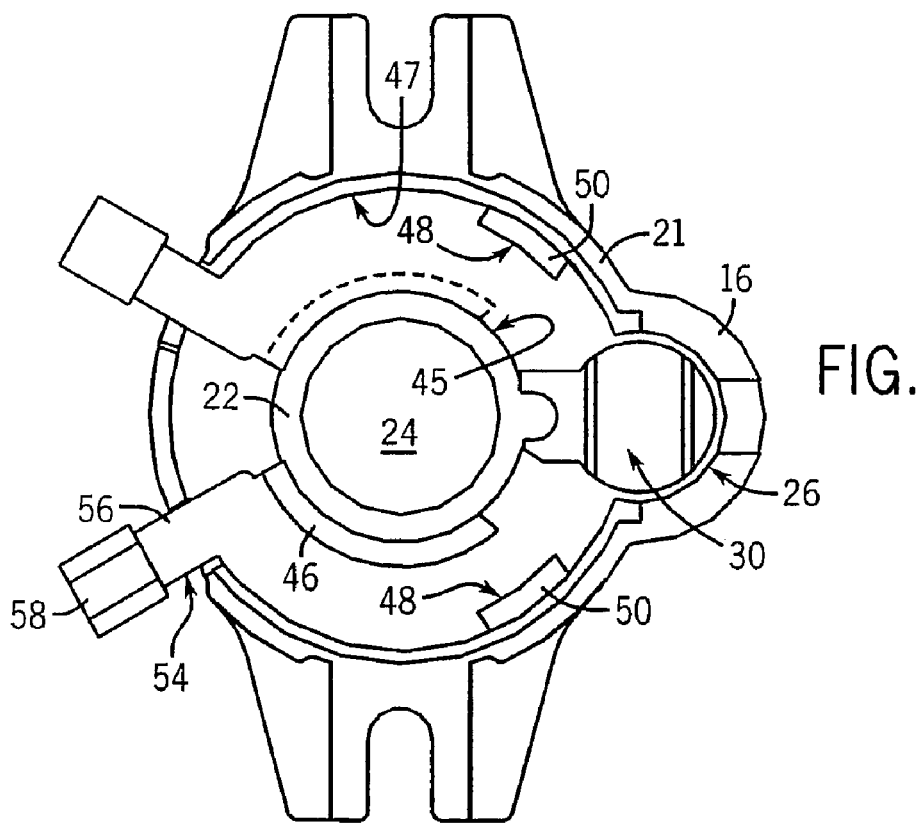
FIG. 4 is a bottom plan view of the heater of FIG. 3.
Figure 5:
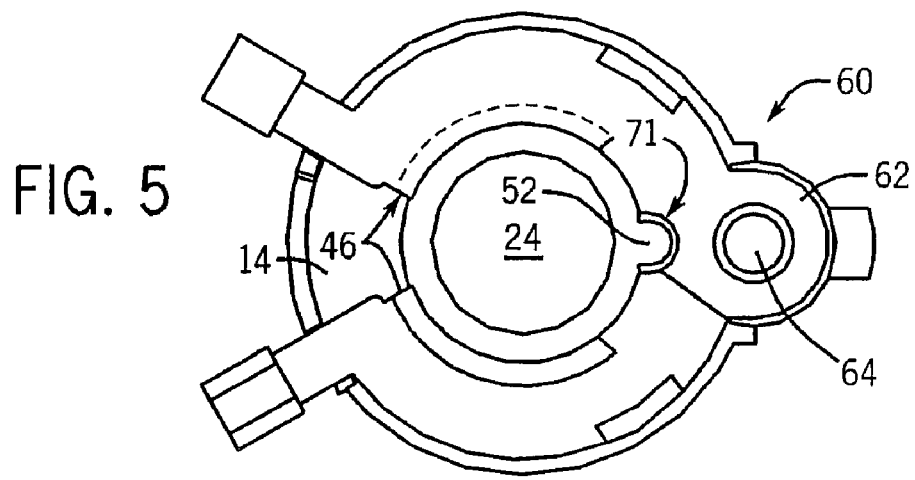
FIG. 5 is a top plan view of the heater of FIG. 1, in assembled form, albeit with its cover removed.

Spring 30 is preferably constructed of steel and of a size that is sufficiently resilient to continuously maintain direct contact between the contacts 34, 36 and the PTC heating element 28, yet not so much as to deform the element 28. As shown in FIG. 6, the spring 30 is comprised of a generally circular belly portion 66 and two legs 68. The legs defined between them a notch that also receives projection 52 for alignment purposes. There is also a foot 72 that can catch between the contacts and the inner wall for further alignment and anchoring. Compressing the bulging section 38 creates a spring resistance.

The contacts are kept sufficiently separate from each other where vertically aligned to reduce the risk of short circuiting. Also, where they are not vertically aligned the separation is even greater.

The accommodation of thermal expansion is achieved without the complexity of conventional spring installation techniques. Further, the parts are properly and reliably mounted, and there is no need for the use of rivets to assemble the housing.

While the preferred embodiment has been described above, it should be appreciated that there are other embodiments of the invention within the spirit and scope of this disclosure. For example, the device can be powered by a different source of energy (e.g. battery power or a solar power panel), and other shapes of contacts can be used. Hence, the invention is not to be limited to just the specific embodiments shown or described.

INDUSTRIAL APPLICABILITY

The invention provides improved heaters for use with a dispenser of volatile air treatment chemicals, particularly those having improved electrical contacts and springs.

What is claimed is:

1. A heater suitable for use with an air treatment chemical dispenser, the heater comprising:
    a housing having a base and a cover, the base and cover together defining an internal generally ring-shaped cavity and an axial through bore;
    a first arc-shaped electrical contact positioned in the cavity;
    a second arc-shaped electrical contact also positioned in the cavity and having a portion overlapping the first arc-shaped electrical contact, and having another portion which does not overlap the first arc-shaped electrical contact;
    a heating element sandwiched between the first and second electrical contacts at a position where the first and second electrical contacts overlap; and
    a spring positioned adjacent at least one of the first and second electrical contacts to bias that contact towards the heating element while also allowing for adjustment if thermal expansion of the housing occurs when the heating element is generating heat;
    wherein the first and second arc-shaped electrical contacts do not overlap over a majority of a plan view area of the first arc-shaped electrical contact.

2. The heater of claim 1, wherein the first and second electrical contacts are made of metal which is both electrically conductive and heat conductive.

3. The heater of claim 1, wherein the first and second electrical contact are both made of aluminum and at least one of the first and second electrical contacts is formed with a raised platform adjacent the heating element.

4. A heater suitable for use with an air treatment chemical dispenser, the heater comprising:
    a housing having a base and a cover, the base and cover together defining an internal generally ring-shaped cavity and an axial through bore;
    a first arc-shaped electrical contact positioned in the cavity;
    a second arc-shaped electrical contact also positioned in the cavity and having a portion overlapping the first arc-shaped electrical contact, and having another portion which does not overlap the first arc-shaped electrical contact; and
    a heating element sandwiched between the first and second electrical contacts at a position where the first and second electrical contacts overlap;
    wherein the first and second arc-shaped electrical contacts do not overlap over a majority of a plan view area of the first arc-shaped electrical contact; and
    wherein at least one of the first and second electrical contacts is formed with a portion that bends in an axial direction along the through bore.

5. A heater suitable for use with an air treatment chemical dispenser, the heater comprising:
    a housing having a base and a cover, the base and cover together defining an internal generally ring-shaped cavity and an axial through bore;
    a first arc-shaped electrical contact positioned in the cavity;
    a second arc-shaped electrical contact also positioned in the cavity and having a portion overlapping the first arc-shaped electrical contact, and having another portion which does not overlap the first arc-shaped electrical contact; and
    a heating element sandwiched between the first and second electrical contacts at a position where the first and second electrical contacts overlap;
    wherein the first and second arc-shaped electrical contacts do not overlap over a majority of a plan view area of the first arc-shaped electrical contact;

wherein the first and second electrical contacts extend on opposite sides of the through bore; and wherein at least one of the first and second electrical contacts has an alignment notch which interfits with an alignment projection from the housing.

6. The heater of claim 5, further comprising a spring that also has an alignment notch that interfits with that alignment projection of the housing.

7. The heater of claim 1, wherein both of the first and second electrical contacts further comprise a crimping terminal.

8. The heater of claim 7, wherein both of the first and second electrical contacts comprise a generally circular contact portion for sandwiching the heating element.

9. A heater suitable for use with an air treatment chemical dispenser, the heater comprising:

a housing having a base and a cover, the base and cover together defining an internal generally ring-shaped cavity and an axial through bore;

a first arc-shaped electrical contact positioned in the cavity;

a second arc-shaped electrical contact also positioned in the cavity and having a portion overlapping the first arc-shaped electrical contact, and having another portion which does not overlap the first arc-shaped electrical contact; and a heating element sandwiched between the first and second electrical contacts at a position where the first and second electrical contacts overlap;

wherein the first and second arc-shaped electrical contacts do not overlap over a majority of a plan view area of the first arc-shaped electrical contact;

wherein the heating element is a positive temperature coefficient pill-shaped heating element;

wherein the heating element is comprised of:

a pill-shaped ceramic portion having first and second opposed facing surfaces;

a first conductive layer formed on the first facing surface; and a second conductive layer formed on the second facing surface;

wherein the heating element is positioned in a radially outwardly projecting alcove of the housing.

10. The heater of claim 1, wherein the base and cover are welded together to essentially enclose the cavity, first and second electrical contacts and heating element.

* * * * *